US012774265B2

(12) United States Patent
Beaudegnies et al.

(10) Patent No.: US 12,774,265 B2
(45) Date of Patent: Oct. 27, 2026

(54) ONE STEP PROCESS FOR THE PREPARATION OF PHENYL ETHYL AMINE DERIVATIVES

(71) Applicant: SYNGENTA CROP PROTECTION AG, Basel (CH)

(72) Inventors: Renaud Beaudegnies, Stein (CH); Helmars Smits, Stein (CH); Christof Teichmann, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 911 days.

(21) Appl. No.: 17/782,467

(22) PCT Filed: Dec. 3, 2020

(86) PCT No.: PCT/EP2020/084510

§ 371 (c)(1),
(2) Date: Jun. 3, 2022

(87) PCT Pub. No.: WO2021/110859

PCT Pub. Date: Jun. 10, 2021

(65) Prior Publication Data

US 2023/0095589 A1 Mar. 30, 2023

(30) Foreign Application Priority Data

Dec. 5, 2019 (EP) .................................... 19213781

(51) Int. Cl.
*C07C 209/16* (2006.01)

(52) U.S. Cl.
CPC .................................. *C07C 209/16* (2013.01)

(58) Field of Classification Search
USPC .......................................................... 564/478
See application file for complete search history.

(56) References Cited

U.S. PATENT DOCUMENTS

| | | | | |
|---|---|---|---|---|
| 6,022,894 | A | 2/2000 | Del Mar et al. | |
| 2008/0293710 | A1 | 11/2008 | Aven | |
| 2011/0195954 | A1 * | 8/2011 | Gottschling ............ | A61P 17/04<br>514/213.01 |

FOREIGN PATENT DOCUMENTS

| | | | |
|---|---|---|---|
| EP | 0372586 | A2 | 6/1990 |
| JP | 6-340592 | A | 12/1994 |
| JP | 2007-537188 | A | 12/2007 |

OTHER PUBLICATIONS

Written Opinion of the International Searching Authority and International Search Report of International Application No. PCT/EP2020/084510, mailed Feb. 17, 2021.
European Search Report for EP Application No. 19213781.8, mailed Apr. 14, 2020.
Adams, M. H. et al., The synthesis of new bronchodilator prodrugs, Synthetic Communications, vol. 29, No. 14, 1999, pp. 2419-2430.
Dokli, et al., "Mechanochemical Ritter Reaction: A Rapid Approach to Functionalized Amides at Room Temperature", Full Paper, European Journal of Organic Chemistry, 2015.
English translation of Office Action for Japanese Patent Application No. 2022-532876, mailed Dec. 25, 2024.5 pages.

* cited by examiner

*Primary Examiner* — Ana Z Muresan
(74) *Attorney, Agent, or Firm* — BakerHostetler; Toni-Junell Herbert

(57) ABSTRACT

The present invention relates to a novel process for the preparation of phenyl ethyl amine derivatives by reacting a phenyl ethyl hydroxy compound with hydrogen cyanide followed by in situ hydrolysis.

18 Claims, No Drawings

ONE STEP PROCESS FOR THE PREPARATION OF PHENYL ETHYL AMINE DERIVATIVES

CROSS-REFERENCE TO RELATED APPLICATIONS

This application is a 371 National Stage application of International Application No. PCT/EP2020/084510 filed Dec. 3, 2020, which claims the benefit of EP 19213781.8, filed Dec. 5, 2019, the entire contents of these applications are hereby incorporated by reference.

The present invention relates to a novel process for the preparation of phenyl ethyl amine derivatives by reacting a phenyl ethyl hydroxy compound with hydrogen cyanide followed by in situ hydrolysis.

The preparation of phenyl ethyl amine derivatives from phenyl ethyl hydroxy compounds has been described before. For example, it is known that compounds of formula (I) (see Scheme 1) may be prepared by reacting a compound of formula (II) with acetonitrile or chloroacetonitrile and then isolating the corresponding acetamide. These acetamide intermediates are then further hydrolysed to the amines of formula (I). Such hydrolysis reactions can be difficult and low yielding due to the relative stability of the acetamide intermediates. Isolating a formyl derivative of formula (III) has also been reported. For example, F. Rachinskii (Zhurnal Obshchei Khimii, 1954, 24, 272) reported that phenyl ethyl amines can be prepared by reacting phenyl ethyl hydroxy compounds of formula (II) with hydrogen cyanide under acidic conditions and then isolating the formyl derivative of formula (III) as shown in Scheme 1. This formyl derivative of formula (III) is then further reacted with a strong acid to give the phenyl ethyl amine of formula (I). A similar reaction was also reported by J. Ritter (Organic Syntheses, 1964, 44, 44) where the isolated formyl derivative of formula (III) was then hydrolysed with a strong base to yield the phenyl ethyl amine of formula (I).

Scheme 1

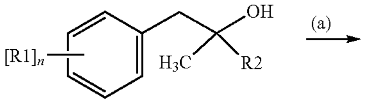

(II)

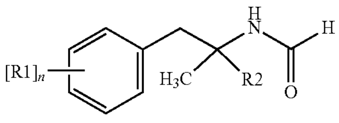

(III)

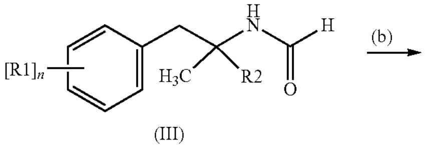

(III)

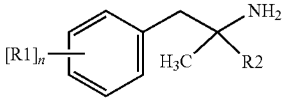

(I)

wherein R1 is independently selected from halogen, nitro, cyano, formyl, C1-C5 alkyl, C2-C5 alkenyl, C2-C5 alkynyl, C3-C6 cycloalkyl, C1-C5 alkoxy, C3-C5 alkenyloxy, C3-C5 alkynyloxy and C1-5 alkylthio, wherein the alkyl, cycloalkyl, alkenyl, alkynyl, alkoxy, alkenyloxy, alkynyloxy and alkylthio is unsubstituted or substituted with 1 to 5 substituents independently selected from halogen, C1-C3 alkyl, C1-C3 alkoxy, cyano and C1-C3 alkylthio; n is 0, 1, 2, 3, 4 or 5; R2 is selected from $C_1$-$C_5$ alkyl, $C_3$-$C_5$ cycloalkyl and $C_2$-$C_5$ alkenyl, wherein $C_1$-$C_5$ alkyl, $C_3$-$C_5$ cycloalkyl and $C_2$-$C_5$ alkenyl are unsubstituted or substituted with 1 to 4 substituents independently selected from halogen, cyano, $C_1$-$C_3$ alkyl and $C_1$-$C_3$ alkoxy.

Step (a) of Scheme 1 is also known as the Ritter reaction. Step (b) of Scheme 1 is the hydrolysis reaction converting the compound of formula (III) to the compound of formula (I). As mentioned above, the prior art teaches that in order to obtain compounds of formula (I), a compound of formula (III) or analogous acetamides has to be isolated first and then reacted in a step (b) under strong acidic or basic conditions. The acid and base in step (b) acts as catalyst for the hydrolysis of the amide group of compounds of formula (III). This reaction leads generally to an overall low yield of compound of formula (I) due to this two-step reaction which includes the isolation of compound of formula (III). For example, F. Rachinskii (Zhurnal Obshchei Khimii, 1954, 24, 272) reported an overall yield of compounds of formula (I) of only around 40% and J. Ritter (Organic Syntheses, 1964, 44, 44) reported an overall yield of compound of formula (I) of only around 55%. Furthermore, another problem besides of the low yield for compounds of formula (I) and the amount of work involved in having two separate reaction steps is the necessity of using severe reaction conditions for step (b), in particular for acetamide intermediates. For example, F. Rachinskii (Zhurnal Obshchei Khimii, 1954, 24, 272) reported that the compound of formula (III) was vigourously boiled in concentrated hydrochloric acid for 16 hours, and J. Ritter (Organic Syntheses, 1964, 44, 44) reported that the compound of formula (III) was heated for at least 2.5 hours in 20% sodium hydroxide solution under reflux. Such conditions pose a safety risk when running the reaction, in particular in large scale, and makes waste disposal more difficult. Hence, there is a need of providing compounds of formula (I) from compounds of formula (II) via a novel improved process. It is the subject matter of the current invention to provide such a novel improved process to obtain compounds of formula (I).

Thus, there is provided a process for the preparation of a compound of formula (I)

(I)

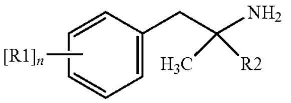

wherein R1 is independently selected from halogen, nitro, cyano, formyl, C1-C5 alkyl, C2-C5 alkenyl, C2-C5 alkynyl, C3-C6 cycloalkyl, C1-5 alkoxy, C3-C5 alkenyloxy, C3-C5 alkynyloxy and C1-C5 alkylthio, wherein the alkyl, cycloalkyl, alkenyl, alkynyl, alkoxy, alkenyloxy, alkynyloxy and alkylthio is unsubstituted or substituted with 1 to 5 substituents independently selected from halogen, C1-C3 alkyl, C1-C3 alkoxy, cyano and C1-C3 alkylthio; n is 0, 1, 2, 3, 4 or 5; R2 is selected from $C_1$-$C_5$ alkyl, $C_3$-$C_5$ cycloalkyl and $C_2$-$C_5$ alkenyl, wherein $C_1$-$C_5$ alkyl, $C_3$-$C_5$ cycloalkyl and $C_2$-$C_5$ alkenyl are unsubstituted or substituted with 1 to 4 substituents independently selected from halogen, cyano, $C_1$-$C_3$ alkyl and $C_1$-$C_3$ alkoxy;

said process comprising reacting a compound of formula (II)

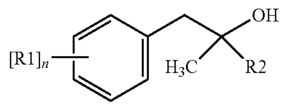

(II)

wherein R1, n and R2 are as defined for a compound of formula (I), with (a) hydrogen cyanide under acidic conditions, followed by (b) subsequent addition of water into the reaction mixture to obtain a compound of formula (I).

It has surprisingly been found that after reacting a compound of formula (II) with hydrogen cyanide under acidic conditions, the addition of water to the reaction mixture led to the formation of compound of formula (I) with high yield. This means that instead of using two reaction steps only one reaction step was used and the reaction was carried out under much milder conditions than reported in the prior art. Hence, a so-called "one pot" reaction for obtaining a compound of formula (I) has surprisingly been found with multiple advantages compared to the prior art teachings. For example, the processing conditions are far less severe which leads to improvements in terms of safety. Furthermore, there is less work-up to be done to obtain a compound of formula (I) which leads to commercially more attractive processes with less waste products.

A skilled person understands how the reaction conditions for the Ritter-type reaction, i.e. from a compound of formula (II) to a compound of formula (III), can be adjusted to obtain transformation from compounds of formula (II) to compounds of formula (III). However, this transformation is typically carried out by the addition of a cyanide salt such as potassium or sodium cyanide to a suitable solvent such as acetic acid, and then mixing this with a strong acid such as sulfuric acid. The compound of formula (II) is then added to this reaction mixture and the temperature increased to a suitable temperature. The reaction temperature of the hydrogen cyanide reaction mixture before the addition of a compound of formula (II) is typically kept between 20° C. and 80° C., preferably between 50° C. and 70° C.

The compound of formula (II) is then added into the reaction mixture. The strong acid such as sulfuric acid may either be added into the reaction mixture simultaneously with the compound of formula (II) or before or after the addition of the compound of formula (II). After the addition of the compound of formula (II) the temperature of the acidic reaction mixture is adjusted to 50° C. to 100° C., preferably to 60° C. to 90° C., even more preferably to 70° C. to 90° C. This temperature range is preferably maintained for a suitable time for the Ritter-type transformation.

After the transformation to a compound of formula (III) in the reaction mixture, a suitable amount of water is added to the reaction mixture. This leads to the transformation of a compound of formula (III) to a compound of formula (I). Preferably, the reaction mixture is charged with 1-50 mole equivalents of water relative to the compound of formula (II), more preferably with 5-20 mole equivalents. The reaction is preferably carried out at an elevated temperature, for example between 75° C. and 100° C., more preferably between 90° C. and 100° C.

A skilled person is aware how to monitor the progress of the reaction and adjust the duration of the reactions accordingly. The obtained compound of formula (I) is worked up in the typical manner well known to persons skilled in the art. For example, compound of formula (I) may be extracted with a suitable organic solvent such as methyl tert-butyl ether (MTBE).

A skilled person understands that a variety of phenyl ethyl amine derivatives may be prepared according to the process of the current invention. Compounds of formula (II) are either commercially available or may be prepared according to literature methods. For example, a compound of formula (II) may be prepared as given in Scheme 2

Scheme 2

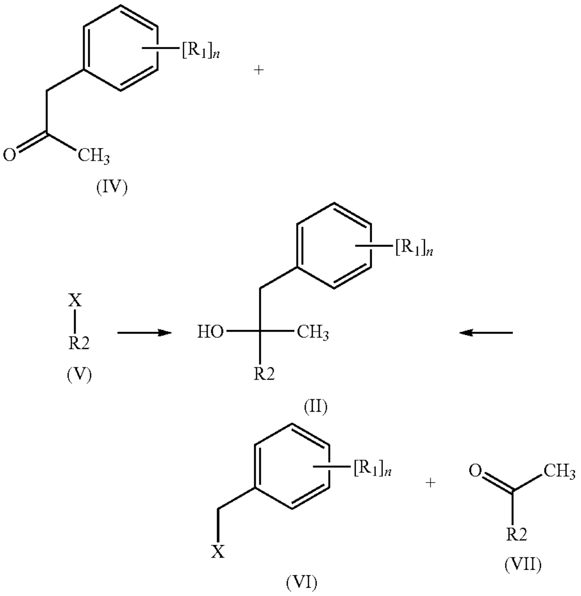

(IV) (V) (II) (VI) (VII)

wherein R1, R2 and n are as defined in Scheme 1. Compounds of formula (II) may be prepared from carbonyl compounds of formula (IV) or (VII) by treatment with an organometallic species of formula (V) or (VI) respectively where X is lithium, an aluminum- or a magnesium-salt, in an inert solvent like diethyl ether at temperatures between −90° C. and 60° C.

In a preferred embodiment of the invention, there is provided a process for the preparation of a compound of formula (I) wherein R1 is independently selected from halogen, cyano, C1-C3 alkyl, C2-C3 alkenyl, C2-C3 alkynyl, cyclopropyl, methoxy, allyloxy, propargyloxy and C1-C2 alkylthio, wherein the alkyl, cyclopropyl, alkenyl, alkynyl, methoxy, allyloxy, propargyloxy and alkylthio are unsubstituted or substituted with 1 to 3 substituents independently selected from fluoro, chloro, methyl and cyano; n is 0, 1, 2 or 3. More preferably, R1 is independently selected from fluoro, bromo, chloro, cyano, methyl and methoxy wherein the methyl and methoxy are unsubstituted or substituted with 1 to 3 substituents independently selected from fluoro, bromo and chloro; n is 0, 1 or 2. Even more preferably, R1 is independently selected from fluoro, bromo and chloro; n is 0 or 1. Most preferably, n is 0 or 1 and when n is 1, then R1 is fluoro, bromo or chloro and attached at the ortho (1-position) or meta (2-position) position of the phenyl ring, preferably at the ortho position.

In a further preferred embodiment of the invention, there is provided a process for the preparation of a compound of formula (I) wherein R2 is selected from $C_1$-$C_5$ alkyl and $C_3$-$C_5$ cycloalkyl, wherein the $C_1$-$C_5$ alkyl and C3-C5 cycloalkyl are unsubstituted or substituted with 1 to 4 substituents independently selected from halogen. More preferably, R2 is $C_1$-$C_5$ alkyl, wherein the $C_1$-$C_5$ alkyl is unsubstituted or substituted with 1 or 3 fluoro substituents. Even more preferably, R2 is selected from methyl, ethyl, n-propyl, isopropyl, isobutyl, $—CH_2CF_3$, $—CH_2—C(CH_3)_3$, $—CH_2—C(CH_3)_2F$ and $—CH_2—C(CH_3)F_2$. Most preferably, R2 is selected from methyl, ethyl, n-propyl, isopropyl and isobutyl.

The current invention includes any combination of the preferred R1, n and R2.

Definitions

The term "alkyl" as used herein—in isolation or as part of a chemical group—represents straight-chain or branched hydrocarbons, preferably with 1 bis 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Alkyl groups with 1 to 4 carbon atoms are preferred, for example methyl, ethyl, n-propyl, isopropyl, n-butyl, isobutyl, s-butyl or t-butyl.

The term "alkenyl"—in isolation or as part of a chemical group—represents straight-chain or branched hydrocarbons, preferably with 2 bis 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1, 1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1, 1,2-trimethyl-2-propenyl, 1-ethyl-1-methyl-2-propenyl and 1-ethyl-2-methyl-2-propenyl. Alkenyl groups with 2 to 4 carbon atoms are preferred, for example 2-propenyl, 2-butenyl or 1-methyl-2-propenyl.

The term "alkynyl"—in isolation or as part of a chemical group—represents straight-chain or branched hydrocarbons, preferably with 2 bis 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Alkynyls with 2 to 4 carbon atoms are preferred, for example ethynyl, 2-propynyl or 2-butynyl-2-propenyl.

The term "cycloalkyl"-in isolation or as part of a chemical group—represents saturated or partially unsaturated mono-, bi- or tricyclic hydrocarbons, preferably 3 to 10 carbon atoms, for example cyclopropyl, cyclobutyl, cyclopentyl, cyclohexyl, cycloheptyl, cyclooctyl, bicyclo[2.2.1]heptyl, bicyclo[2.2.2]octyl or adamantyl.

The term "halogen" or "halo" represents fluoro, chloro, bromo or iodo, particularly fluoro, chloro or bromo. The chemical groups which are substituted with halogen, for example haloalkyl, halocycloalkyl, haloalkyloxy, haloalkylsulfanyl, haloalkylsulfinyl or haloalkylsulfonyl are substituted one or up to the maximum number of substituents with halogen. If "alkyl", "alkenyl" or "alkynyl" are substituted with halogen, the halogen atoms can be the same or different and can be bound at the same carbon atom or different carbon atoms.

The term "in situ" as used herein refers to carrying out the reaction directly in the reaction mixture without isolating the intermediate compound. This means that "in situ" refers to a so-called "one pot reaction" as compared to a two steps reaction.

EXPERIMENTAL

Examples

The following examples are intended to illustrate the invention and are not to be construed as being limitations thereon.

Compound Synthesis and Characterisation The following abbreviations are used throughout this section: s=singlet; bs=broad singlet; d=doublet; dd=double doublet; dt=double triplet; bd=broad doublet; t=triplet; td=triplet doublet; bt=broad triplet; tt=triple triplet; q=quartet; m=multiplet; Me=methyl; Et=ethyl; Pr=propyl; Bu=butyl; DME=1,2-dimethoxyethane; THF=tetrahydrofuran.

Example 1: 2-Methyl-1-phenyl-propan-2-amine

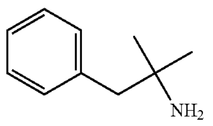

A suspension of potassium cyanide (0.135 g, 1.997 mmol) in acetic acid (0.22 mL, 3.861 mmol) was prepared and cooled with an ice/water bath to 0-10° C. In the meanwhile a mixture of sulfuric acid (0.255 mL, 4.527 mmol) and acetic acid (0.22 mL, 3.861 mmol) was prepared. A strong exothermic effect was observed. Then the acidic solution was added dropwise to the suspension over 5 min. The reaction mixture changed into a milky suspension. 2-methyl-1-phenyl-propan-2-ol (0.2 g, 1.331 mmol) was added drop wise to the suspension over 5 min and the reaction mixture was heated to 80° C. After 3 h stirring at this temperature water (0.240 mL, 13.314 mmol) was added in one portion and it was stirred over night at 80° C.

The cooled down reaction mixture was poured slowly on cold sat. Na2CO3-solution. A gas formation could be observed during the addition as expected. It was extracted 3× with tert-butyl methyl ether.

The organic layers were combined, washed once with brine and dried over $Na_2SO4$. It was filtered and evaporated to obtain 2-methyl-1-phenyl-propan-2-amine with a purity of 93.0% and 89.2% chemical yield.

$^1H$ NMR (400 MHz, $CDCl_3$) δ ppm 1.15 (s, 6H) 1.49 (br s, 2H) 2.69 (s, 2H) 7.19-7.36 (m, 5H)

Example 2: 1-(2-Fluorophenyl)-2-methyl-propan-2-amine

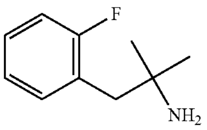

Procedure as above for Example 1. 1-(2-Fluorophenyl)-2-methyl-propan-2-amine was obtained with a purity of 72% and 61.6% chemical yield.

$^1H$ NMR (400 MHz, $CDCl_3$) δ ppm 1.17 (d, 6H) 1.64 (br s, 2H) 2.75 (d, 2H) 7.00-7.18 (m, 2H) 7.19-7.26 (m, 2H)

Example 3: 1-(2-Chlorophenyl)-2-methyl-propan-2-amine

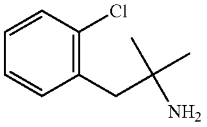

Procedure as above for Example 1. 1-(2-Chlorophenyl)-2-methyl-propan-2-amine was obtained with a purity of 86% and 87.6% chemical yield.

$^1H$ NMR (400 MHz, $CDCl_3$) δ ppm 1.20 (s, 6H) 1.61 (br s, 2H) 2.91 (s, 2H) 7.16-7.33 (m, 3H) 7.35-7.45 (m, 1H)

Example 4: 1-(3-Fluorophenyl)-2-methyl-propan-2-amine

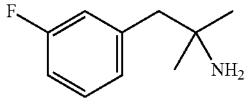

Procedure as above for Example 1. 1-(3-Fluorophenyl)-2-methyl-propan-2-amine was obtained with a purity of 39% and 24.3% chemical yield.

$^1H$ NMR (400 MHz, $CDCl_3$) δ ppm 1.26 (s, 6H) 2.78-2.87 (m, 2H) 3.71-3.99 (br s, 2H) 6.90-7.05 (m, 3H) 7.23-7.33 (m, 1H)

Example 5: 2-Methyl-1-(o-tolyl)propan-2-amine

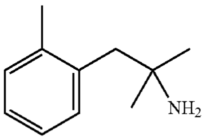

Procedure as above for Example 1. 2-Methyl-1-(o-tolyl)propan-2-amine was obtained with a purity of 64.4% and 58.9% chemical yield.

$^1H$ NMR (400 MHz, $CDCl_3$) δ ppm 1.18 (s, 6H) 1.66 (br s, 2H) 2.39 (s, 3H) 2.77 (s, 2H) 7.13-7.22 (m, 4H)

Example 6: 1-(2-bromophenyl)-2-methyl-propan-2-amine

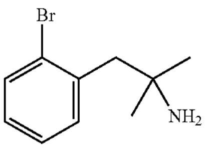

Procedure as above for Example 1. 1-(2-Bromophenyl)-2-methyl-propan-2-amine was obtained with a purity of 72.9% and 73.2% chemical yield.

$^1H$ NMR (400 MHz, $CDCl_3$) δ ppm 1.22 (s, 6H) 1.73 (br s, 2H) 2.95 (s, 2H) 7.08-7.15 (m, 1H) 7.23-7.35 (m, 2H) 7.59 (d, 1H)

Example 7: 2-Methyl-1-phenyl-butan-2-amine

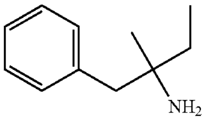

Procedure as above for Example 1. 2-Methyl-1-phenyl-butan-2-amine was obtained with a purity of 83% and 78.1% chemical yield.

$^1H$ NMR (400 MHz, $CDCl_3$) δ ppm 0.96-1.02 (m, 3H) 1.05 (s, 3H) 1.34-1.51 (m, 4H) 2.68 (s, 2H) 7.17-7.36 (m, 5H)

Example 8: 2-Methyl-1-phenyl-pentan-2-amine

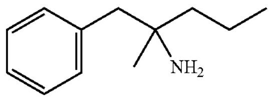

Procedure as above for Example 1. 2-Methyl-1-phenyl-pentan-2-amine was obtained with a purity of 86% and 31.7% chemical yield.

$^1H$ NMR (400 MHz, $CDCl_3$) δ ppm 0.96 (t, 3H) 1.12 (s, 3H) 1.36-1.53 (m, 4H) 2.71 (br s, 2H) 2.74 (s, 2H) 7.19-7.35 (m, 5H)

Example 9: 2,4-Dimethyl-1-phenyl-pentan-2-amine

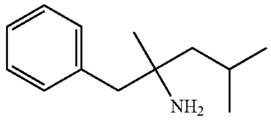

Procedure as above for Example 1. 2,4-Dimethyl-1-phenyl-pentan-2-amine was obtained with a purity of 93% and 85.0% chemical yield.

$^1$H NMR (400 MHz, $CDCl_3$) δ ppm 1.01 (dd, 6H) 1.08 (s, 3H) 1.2 (brs, 2H) 1.37 ((qd)m, 2H) 1.83-1.93 (m, 1H) 2.65-2.72 (m, 2H) 7.19-7.35 (m, 5H)

Example 10:
1-(3-Fluorophenyl)-2,4-dimethyl-pentan-2-amine

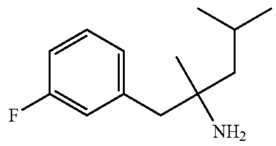

Procedure as above for Example 1. 1-(3-Fluorophenyl)-2,4-dimethyl-pentan-2-amine was obtained with a purity of 57% and 43.9% chemical yield.

$^1$H NMR (400 MHz, $CDCl_3$) δ ppm 1.01 (dd, 6H) 1.09 (s, 3H) 1.28-1.44 (m, 4H) 1.84-1.90 (m, 1H) 2.68 (s, 2H) 6.92-7.00 (m, 3H) 7.27 (m, 1H)

The invention claimed is:

1. A process for preparation of a compound of formula (I)

(I)

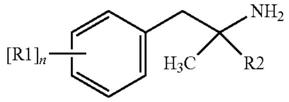

wherein

R1 is independently selected from the group consisting of halogen, nitro, cyano, formyl, C1-C5 alkyl, C2-C5 alkenyl, C2-C5 alkynyl, C3-C6 cycloalkyl, C1-C5 alkoxy, C3-C5 alkenyloxy, C3-C5 alkynyloxy and C1-C5 alkylthio, wherein the alkyl, cycloalkyl, alkenyl, alkynyl, alkoxy, alkenyloxy, alkynyloxy and alkylthio is unsubstituted or substituted with 1 to 5 substituents independently selected from halogen, C1-C3 alkyl, C1-C3 alkoxy, cyano and C1-C3 alkylthio;

n is 0, 1, 2, 3, 4 or 5; and

R2 is selected from the group consisting of C1-C5 alkyl, C3-C5 cycloalkyl and C2-C5 alkenyl, wherein C1-C5 alkyl, C3-C5 cycloalkyl and C2-C5 alkenyl are unsubstituted or substituted with 1 to 4 substituents independently selected from halogen, cyano, C1-C3 alkyl and C1-C3 alkoxy;

said process comprising:

reacting a compound of formula (II)

(II)

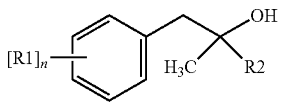

wherein R1, n and R2 are as defined for the compound of formula (I), with (a) a cyanide under acidic conditions to form a reaction mixture, followed by (b) heating the reaction mixture to an elevated temperature and in situ subsequent addition of water into the reaction mixture of step (a) at the elevated temperature for a period of time, wherein the elevated temperature is between 75° C. and 100° C.; and obtaining the compound of formula (I).

2. The process according to claim 1, wherein

R1 is independently selected from the group consisting of fluoro, bromo, chloro, cyano, methyl and methoxy wherein the methyl and methoxy are unsubstituted or substituted with 1 to 3 substituents independently selected from fluoro and chloro;

n is 0, 1 or 2; and

R2 is selected from the group consisting of C1-C5 alkyl and C3-C5 cycloalkyl, wherein the C1-C5 alkyl and C3-C5 cycloalkyl are unsubstituted or substituted with 1 to 4 substituents independently selected from halogen.

3. The process according to claim 1, wherein

R1 is independently selected from the group consisting of fluoro, bromo and chloro;

n is 0 or 1; and

R2 is selected from the group consisting of methyl, ethyl, n-propyl, isopropyl, isobutyl, —CH2CF3, —CH2—C (CH3) 3, —CH2—C(CH3) 2F and —CH2—C(CH3) F2.

4. The process according to claim 1, wherein n is 0 or 1; and when n is 1, R1 is fluoro, bromo or chloro and attached at the ortho (1-position) or meta (2-position) position of the phenyl ring; and R2 is selected from the group consisting of methyl, ethyl, n-propyl, isopropyl and isobutyl.

5. The process according to claim 1, wherein the subsequent addition of water comprises 1-50 mole equivalents of water relative to the compound of formula (II).

6. The process according to claim 1, wherein the step (a) is carried out by adding a cyanide salt to a suitable solvent, then adding a strong acid and the compound of formula (II).

7. The process according to claim 6, wherein the cyanide salt is potassium cyanide and the strong acid is sulfuric acid.

8. The process according to claim 1, wherein the elevated temperature comprises a temperature between 80° C. and 100° C.

9. The process according to claim 1, wherein the elevated temperature is about 80° C.

10. The process according to claim 1, wherein the subsequent addition of water in step (b) comprises 5-20 mole equivalents of water relative to the compound of formula (II).

11. The process according to claim 1, wherein the subsequent addition of water in step (b) comprises about 10 mole equivalents of water relative to the compound of formula (II).

12. The process according to claim 1, wherein the subsequent addition of water in step (b) is carried out in one portion.

13. The process according to claim 1, wherein step (b) is carried out overnight at about 80° C.

14. The process according to claim 1, wherein the period of time in step (b) is at least 2.5 hours.

15. The process according to claim 1, wherein the cyanide is a salt.

16. The process according to claim 15, wherein the salt is a potassium salt.

17. A process for preparation of a compound of formula (I)

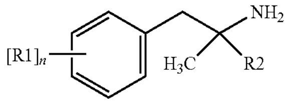

(I)

wherein

R1 is independently selected from the group consisting of halogen, nitro, cyano, formyl, C1-C5 alkyl, C2-C5 alkenyl, C2-C5 alkynyl, $C_3$-$C_6$ cycloalkyl, C1-$C_5$ alkoxy, $C_3$-$C_5$ alkenyloxy, C3-C5 alkynyloxy and C1-C5 alkylthio, wherein the alkyl, cycloalkyl, alkenyl, alkynyl, alkoxy, alkenyloxy, alkynyloxy and alkylthio is unsubstituted or substituted with 1 to 5 substituents independently selected from halogen, C1-C3 alkyl, C1-C3 alkoxy, cyano and C1-C3 alkylthio;

n is 0, 1, 2, 3, 4 or 5; and

R2 is selected from the group consisting of C1-C5 alkyl, C3-C5 cycloalkyl and C2-C5 alkenyl, wherein C1-C5 alkyl, C3-C5 cycloalkyl and C2-C5 alkenyl are unsubstituted or substituted with 1 to 4 substituents independently selected from halogen, cyano, C1-C3 alkyl and C1-C3 alkoxy;

said process comprising:

reacting a compound of formula (II)

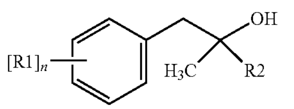

(II)

wherein R1, n and R2 are as defined for the compound of formula (I), with (a) a cyanide under acidic conditions to form a reaction mixture, followed by (b) heating the reaction mixture to an elevated temperature and in situ subsequent addition of water into the reaction mixture of step (a) at the elevated temperature for a period of time, wherein the elevated temperature is between 75° C. and 100° C.; and obtaining the compound of formula (I) without further reactions.

18. A process for preparation of a compound of formula (I)

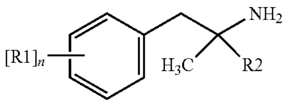

(I)

wherein

R1 is independently selected from the group consisting of halogen, nitro, cyano, formyl, C1-C5 alkyl, C2-C5 alkenyl, C2-C5 alkynyl, C3-C6 cycloalkyl, C1-C5 alkoxy, C3-C5 alkenyloxy, C3-C5 alkynyloxy and C1-C5 alkylthio, wherein the alkyl, cycloalkyl, alkenyl, alkynyl, alkoxy, alkenyloxy, alkynyloxy and alkylthio is unsubstituted or substituted with 1 to 5 substituents independently selected from halogen, C1-C3 alkyl, C1-C3 alkoxy, cyano and C1-C3 alkylthio;

n is 0, 1, 2, 3, 4 or 5; and

R2 is selected from the group consisting of C1-C5 alkyl, C3-C5 cycloalkyl and C2-C5 alkenyl, wherein C1-C5 alkyl, C3-C5 cycloalkyl and C2-C5 alkenyl are unsubstituted or substituted with 1 to 4 substituents independently selected from halogen, cyano, C1-C3 alkyl and C1-C3 alkoxy;

said process comprising:

reacting a compound of formula (II)

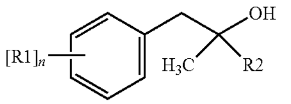

(II)

wherein R1, n and R2 are as defined for the compound of formula (I), with (a) a cyanide under acidic conditions to form a reaction mixture, followed by (b) heating the reaction mixture to an elevated temperature and in situ subsequent addition of water into the reaction mixture of step (a) at the elevated temperature for a period of time, wherein the elevated temperature is between 75° C. and 100° C.; and obtaining the compound of formula (I) without isolating a compound of formula (III)

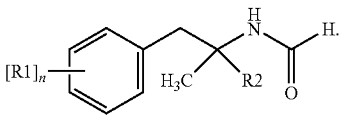

(III)

* * * * *